United States Patent [19]

Yanagisawa et al.

[11] 4,071,681

[45] Jan. 31, 1978

[54] PROCESS FOR PREPARING BETA-LACTAM ANTIBIOTIC SUBSTANCES

[75] Inventors: Hiroaki Yanagisawa; Akiko Ando; Masami Fukushima; Hideo Nakao, all of Tokyo, Japan

[73] Assignee: Sankyo Company Limited, Tokyo, Japan

[21] Appl. No.: 727,696

[22] Filed: Sept. 28, 1976

Related U.S. Application Data

[62] Division of Ser. No. 501,245, Aug. 28, 1974, Pat. No. 4,016,155.

[30] Foreign Application Priority Data

Sept. 7, 1973 Japan ................................ 48-100856

[51] Int. Cl.$^2$ .......................................... C07D 499/04
[52] U.S. Cl. ................................. 542/420; 260/239.1; 260/306.7 C; 542/422; 544/14
[58] Field of Search ....................... 260/240 G, 243 C; 542/420

[56] References Cited

U.S. PATENT DOCUMENTS

| 3,867,379 | 2/1975 | Dolfini et al. | 260/240 G |
| 3,891,629 | 6/1975 | Diassi et al. | 260/240 CX |
| 3,910,902 | 10/1975 | Dolfini et al. | 260/243 C |
| 3,957,081 | 5/1976 | Lund | 260/240 G |

OTHER PUBLICATIONS

Cama, L.D. et al., "Substituted Penicillins and Cephalosporins" in Tetrahedron Letters" pp. 3505-3508 1/1973.

Primary Examiner—Arthur P. Demers
Attorney, Agent, or Firm—Flynn & Frishauf

[57] ABSTRACT

Process for preparing $\beta$-lactam antibiotic substances useful as intermediate for various cephalosporin or penicillin derivatives, which comprises oxidation of 7-benzylideneaminocephem or 6-benzylideneaminopenam compounds capable of being converted to their quinoid forms by oxidation followed by reaction with lower alkanols.

10 Claims, No Drawings

PROCESS FOR PREPARING BETA-LACTAM ANTIBIOTIC SUBSTANCES

This is a division of application Ser. No. 501,245, filed Aug. 28, 1974, now U.S. Pat. No. 4,016,155.

This invention relates to a new process for preparing β-lactam antibiotic substances. More particularly, it relates to a new process for introducing an alkoxy group into a cephem nucleus at the 7-position thereof or a penam nucleus at the 6-position thereof. Still more particularly, it is concerned with a new process for preparing a β-lactam antibiotic substance which comprises oxidation of a 7-benzylideneaminocephem compound or a 6-benzylideneaminopenam compound, both of which are capable of being converted to their quinoid forms by oxidation, followed by reaction with a lower alkanol to form a 7β-benzylideneamino-7α-alkoxycephem compound or a 6β-benzylideneamino-6α-alkoxypenam compound.

More specifically, this invention is concerned with a novel process for preparing a compound having the formula

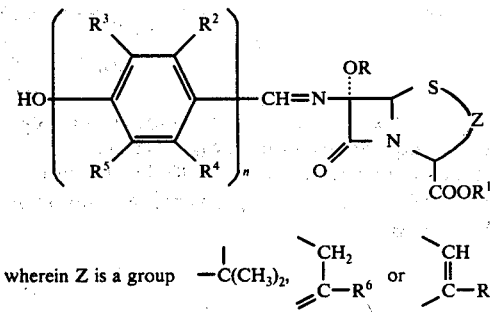

wherein Z is a group $-C(CH_3)_2$, $\begin{matrix}|\\C-R^6\\\|\\CH_2\end{matrix}$ or $\begin{matrix}\\C-R^{6'}\\\|\\CH\end{matrix}$ $R^1$ to $R^6$ are individually groups which do not participate in the reaction, R is a lower alkyl group, and n is an integer of 1 or 2 which comprises oxidation of a compound having the formula

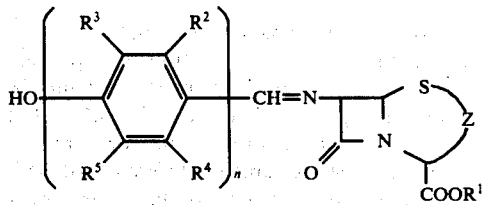

wherein Z, $R^1$ to $R^5$ and n are as defined above and subsequent reaction with a lower alkanol.

For introducing an alkoxy group into a cephem nucleus at its 7-position or into a penam nucleus at its 6-position, the following processes have been proposed in the art.

a. A process of diazotization of 7-aminocephalosporanic acid and subsequent conversion into the corresponding alkoxy derivative (Japanese Patent Provisional Publication 931/1972; Journal of the American Chemical Society, Vol. 94, p. 1408 (1972)).

b. A process of alkylthiolation or fluorination and acylation of a 6- or 7-benzylideneamino compound and subsequent conversion into the alkoxylated compound (Journal of Organic Chemistry, Vol. 38, p. 943 and 2857 (1973)).

c. A process of reaction of a 7-benzylideneamino compound with a dialkyl peroxy compound (Japanese Patent Provisional Publication 42691/1972).

d. A process wherein a 7-acylaminocephem compound or a 6-acylaminopenam compound is subjected to N-chlorination and converted to the corresponding acylimino compound (followed by) addition of methanol (Journal of the American Chemical Society, Vol. 95, p. 2401 and 2403 (1973)).

However, the above-mentioned prior art processes have some drawbacks in that, for instance, many reaction steps and complicated procedures are required with poor yields in the above process (a), and the processes (b) to (d) are industrially inadvantageous due to, e.g., lower temperatures required.

As a result of our research on alkoxylation of a cephem nucleus at its 7-position or a penam nucleus at its 6-position, we have found and developed an improved and simple method which entirely differs from the prior methods and in which by-products are hardly formed and lower temperatures are not required in the reaction procedures.

It is, accordingly, a primary object of this invention to provide a new and improved process for preparing β-lactam antibiotic substances which is entirely different and unexpected from the prior art.

Other objects and advantages of this invention will become apparent from the following disclosure of this invention.

The compounds (I) which may be prepared by the process of this invention are new substances not disclosed in the prior art and useful as an intermediate for the synthesis of various cephalosporin or penicillin derivatives each having a broad antibacterial spectrum.

For instance, the compounds obtained by the process of this invention can be reacted with an acylating agent directly or worked by existing steps, for example, by the action of 2,4-dinitrophenyl hydrazine and p-toluenesulfonic acid to form an 7-amino-7-methoxycephalosporin derivative, which is then reacted with an acylating agent to form a 7-methoxy-7-acylaminocephalosporin derivative followed by the removal of the protective group of the carboxylic acid at 4-position in a conventional manner, whereby a compound having a strong antibacterial activity is produced.

In accordance with the present invention, there is provided, broadly speaking, a new process for preparing a β-lactam antibiotic substance which comprises oxidation of a 7-benzylideneaminocephem compound or a 6-benzylideneaminopenam compound, both of which are capable of being converted to their quinoid forms, followed by reaction with a lower alkanol to form a 7β-benzylideneamino-7α-alkoxycephem compound or a 6β-benzylideneamino-6α-alkoxypenam compound.

Specifically speaking, there is provided a new and advantageous process for preparing a compound having the formula

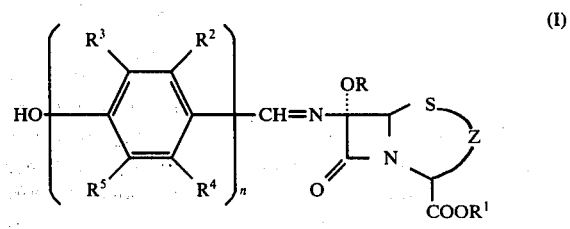

-continued wherein Z is a group 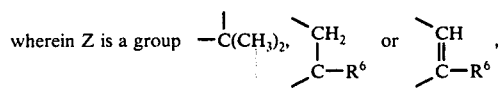, $R^1$ to $R^6$ are individually groups which do not participate in the reaction, R is a lower alkyl group, and $n$ is an integer of 1 or 2 which comprises oxidation of a compound having the formula

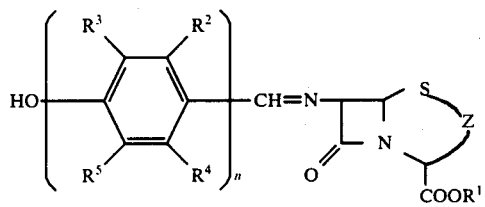
(II)

wherein Z, $R^1$ to $R^5$ and $n$ are as defined above and subsequent reaction with a lower alkanol.

In one more specific aspect of this invention, there is provided a process for preparing a compound having the formula

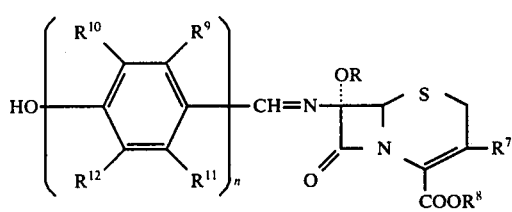
(III)

wherein $R^7$ represents hydrogen atom, methyl group, cyanomethyl group, an acyloxymethyl group, carbamoyloxymethyl group, an alkoxymethyl group, an alkylthiomethyl group or a heterocyclic thiomethyl group, $R^8$ represents a protective group for carboxyl group, $R^9$ to $R^{12}$ may be the same or different and each represents hydrogen atom, a straight or branched lower alkyl group, an alkoxy group, a halogen atom, cyano group or an alkoxycarbonyl group and $R^9$ and $R^{10}$ and $R^{11}$ and $R^{12}$ may form a ring fused with the benzene ring to which they are attached, $n$ is 1 or 2 and R represents a lower alkyl group which comprises oxidation of a cephem compound having the formula

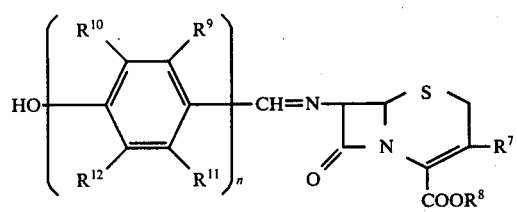
(IV)

wherein $R^7$ to $R^{12}$ and $n$ have the same meanings as defined above and subsequent reaction with a lower alkanol. In a preferred embodiment of this aspect, there is provided a process for preparing a compound having the formula

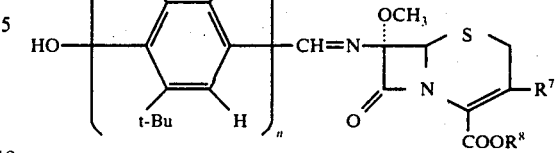
(III-a)

wherein $R^7$ represents hydrogen atom, methyl group, cyanomethyl group, an acyloxymethyl group, carbamoyloxymethyl group, an alkoxymethyl group, an alkylthiomethyl group or a heterocyclic thiomethyl group, $R^8$ represents a protective group for carboxyl group, $n$ is 1 or 2 and t-Bu is tert.-butyl group which comprises oxidation of a compound having the formula

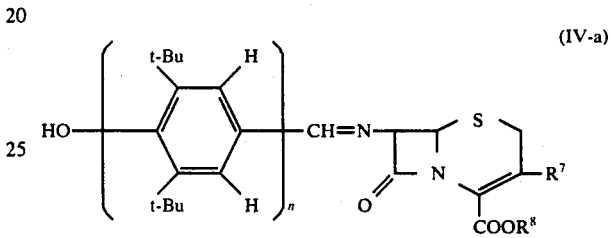
(IV-a)

wherein $R^7$, $R^8$, $n$ and t-Bu have the same meanings as above and subsequent reaction with methanol.

In another more specific aspect of this invention, there is provided a process for preparing a compound having the formula

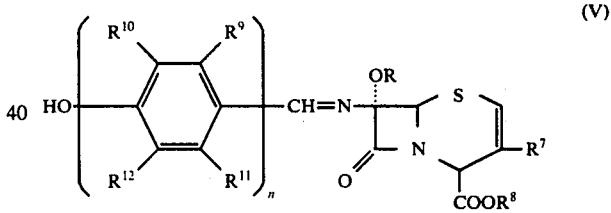
(V)

wherein $R^7$ represents hydrogen atom, methyl group, cyanomethyl group, an acyloxymethyl group, carbamoyloxymethyl group, an alkoxymethyl group, an alkylthiomethyl group or a heterocyclic thiomethyl group, $R^8$ represents a protective group for carboxyl group, $R^9$ to $R^{12}$ may be the same or different and each represents hydrogen atom, a straight or branched lower alkyl group, an alkoxy group, a halogen atom, cyano group or an alkoxycarbonyl group and $R^9$ and $R^{10}$ and $R^{11}$ and $R^{12}$ may form a ring fused with the benzene ring to which they are attached, $n$ is 1 or 2 and R represents a lower alkyl group which comprises oxidation of a cephem compound having the formula

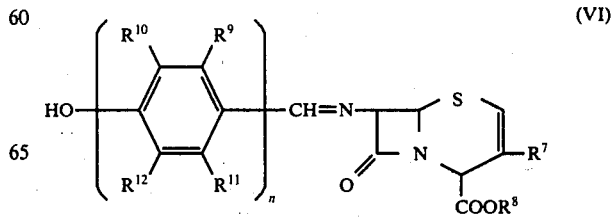
(VI)

wherein $R^7$ to $R^{12}$ and $n$ have the same meanings as defined above and subsequent reaction with a lower alkanol. In a preferred embodiment of this aspect, there is provided a process for preparing a compound having the formula

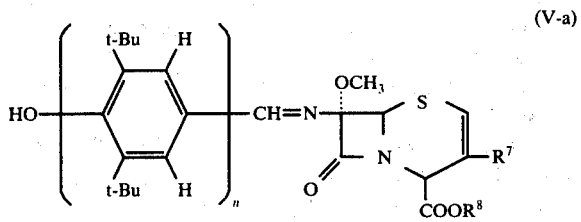

(V-a)

wherein $R^7$ represents hydrogen atom, methyl group, cyanomethyl group, an acyloxymethyl group, carbamoyloxymethyl group, an alkoxymethyl group, an alkylthiomethyl group or a heterocyclic thiomethyl group, $R^8$ represents a protective group for carboxyl group, $n$ is 1 or 2 and t-Bu is tert.-butyl group which comprises oxidation of a compound having the formula

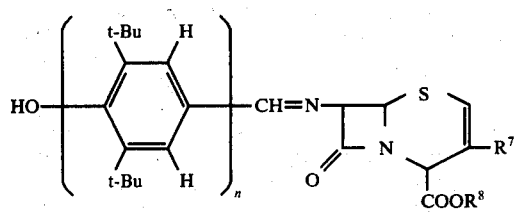

(VI-a)

wherein $R^7$, $R^8$, $n$ and t-Bu have the same meanings as above and subsequent reaction with methanol.

In another aspect of this invention, there is provided a process for preparing a compound having the formula

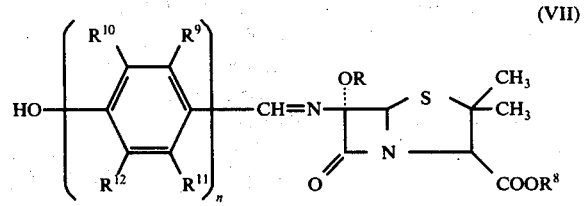

(VII)

wherein $R^8$ represents a protective group for carboxyl group, $R^9$ to $R^{12}$ may be the same or different and each represents hydrogen atom, a lower alkyl group, an alkoxy group, a halogen atom, cyano group or an alkoxycarbonyl group and $R^9$ and $R^{10}$ and $R^{11}$ and $R^{12}$ may form a ring fused with the benzene ring to which they are attached, $n$ is 1 or 2 and R represents a lower alkyl group which comprises oxidation of a penam compound having the formula

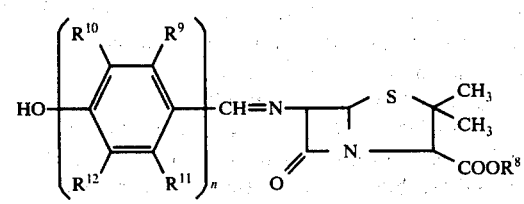

(VIII)

wherein $R^8$ to $R^{12}$ and $n$ have the same meanings as defined above and subsequent reaction with a lower alkanol. In a preferred embodiment of this aspect, there is provided a process for preparing a compound having the formula

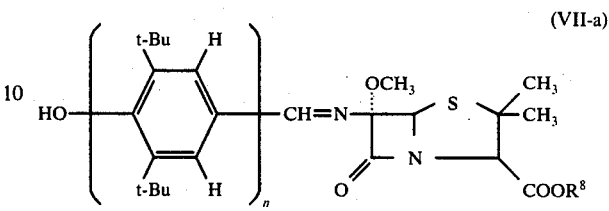

(VII-a)

wherein $R^8$ represents a protective group for carboxyl group, $n$ is 1 or 2 and t-Bu is tert.-butyl group which comprises oxidation of a compound having the formula

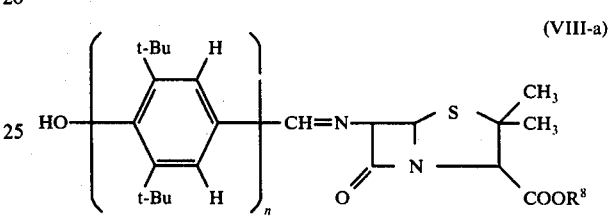

(VIII-a)

wherein $R^8$, $n$ and t-Bu have the same meanings as above and subsequent reaction with methanol.

With regard to the starting material (II) in the process of this invention, the 7-benzylideneaminocephem or 6-benzylideneaminopenam compound capable of being converted to its quinoid form by oxidation means a Schiff base formed by a formyl compound of benzene or a fused aromatic polycyclic hydrocarbon, e.g., naphthalene, anthracene or biphenyl and an 7-aminocephem or 6-aminopenam compound, said benzene or hydrocarbon having hydroxy group at the conjugated position with the formyl group. As the examples of the aforesaid formyl compound are mentioned p-hydroxybenzaldehyde, 4-formyl-1-naphthol, 5-formyl-1-naphthol, 9-formyl-10-hydroxyanthracene, 4-(4-hydroxyphenyl) benzaldehyde and the like. On the benzene ring or fused benzene ring of the above groups may be optionally present any of those substituents that do not participate in the present reaction. Also, on the cephem or penam nucleus may be present the substituents that do not participate in the present reaction. The benzylideneamino group at 7- or 6-position of the cephem or penam nucleus, respectively, may be of α- or β-configuration.

In the above formula, $R^1$ to $R^6$ may be any of those groups that do not participate in the present reaction. As the examples of the group $R^6$ are mentioned the substituents taking the 3-position in previously known natural and synthetic cephem compounds, the representatives thereof being hydrogen atom, methyl group, cyanomethyl group, acyloxymethyl groups such as alkanoyloxymethyl, e.g., acetoxymethyl, propionyloxymethyl, pivaloyloxymethyl or aroyloxymethyl, e.g., benzoyloxymethyl, carbamoyloxymethyl group, alkoxymethyl groups such as methoxymethyl, ethoxymethyl, butyloxymethyl, alkylthiomethyl groups such as methylthiomethyl, ethylthiomethyl, propylthiomethyl, heterocyclic thiomethyl groups such as 2-pyridylthiomethyl, 2-(1,3,5-triazolo)thiomethyl, 3-pyrazolothiomethyl, 1imidazolinylthiomethyl, 5-methyl-1,3,4-thiadiazolyl-2-thiomethyl, 1-methyl-1H-tetrazol-5-ylthiomethyl. The group $R^1$ is a protective group of the carboxyl group in carrying out the process of this invention, including those groups easily removable in subsequent step without destruction of the cephem or penam nucleus and those groups that may remain in the final product. As the examples of such protective group are mentioned a straight or branched lower alkyl group such as methyl, ethyl, propyl, isopropyl, butyl, tert-butyl and substituted methyl groups such as lower alkoxy methyl or benzyloxymethyl groups, e.g., methoxymethyl, ethoxymethyl, benzyloxymethyl, p-nitrobenzyloxymethyl; lower alkanoyloxy lower alkyl groups, e.g., acetoxymethyl, pivaloyloxymethyl, 1-acetoxyethyl, 1-acetoxypropyl, 1-pivaloyloxyethyl; benzoyloxymethyl group; cyanomethyl group; 2,2,2-trichloroethyl group; phthalimidomethyl group; benzyl groups such as benzyl, p-methoxybenzyl, p-nitrobenzyl; benzhydryl group; phenacyl groups such as phenacyl, p-bromophenacyl, p-methoxyphenacyl, p-nitrophenacyl and tri lower alkyl silyl groups such as trimethylsilyl and the like. The groups $R^2$ to $R^5$ may be any of those groups that would not adversely affect the compound having the above-mentioned formula (II) to take its quinoid form. As the examples of such group are mentioned, for instance, hydrogen atom; straight or branched lower alkyl groups such as methyl, ethyl, propyl, isopropyl, tert.-butyl; lower alkoxy groups such as methoxy, ethoxy, propoxy, isopropoxy,tert.-butoxy; halogen atoms such as chlorine, bromine; cyano group; lower alkoxycarbonyl groups such as methoxycarbonyl, ethoxycarbonyl,tert.-butoxycarbonyl and the like. $R^2$ and $R^3$ or $R^4$ and $R^5$ may be linked together to form a ring fused with the benzene ring to which they are attached. $n$ is 1 or 2 and, when $n$ is 2, for example biphenyl, binaphthalene, p-(4-naphthyl)benzene may be formed. Usually, a phenyl group having a sterically hindered alkyl group, e.g., tert.-butyl at orthoposition to the hydroxy group may be suitable used.

As the oxidizing agents which may be employed in the process of this invention may be effectively used any of those agents that could oxidize phenol to a quinoid form without destruction of the cephem or penam nucleus and as the examples of such agents are preferably mentioned metal oxides such as lead dioxide, manganese dioxide and the like; quinone compounds such as benzoquinones having as substituents electron attractive groups, e.g., dichlorodicyanobenzoquinone, chloranil and the like and lead dioxide and dichlorodicyanobenzoquinone are particularly advantageous in view of its easy availability and inexpensiveness and its reactivity.

The lower alkoxy group to be introduced in this invention may be straight or branched and, thus, as the lower alkanol which may be employed in the process of this invention are preferably of 1 to 6 carbon atoms and exemplified by straight or branched lower alkanols such as methanol, ethanol, n-propanol, isopropanol, n-butanol, isobutanol, sec.-butanol, tert.-butanol, n-pentanol, n-hexanol.

The process of this invention consists of a oxidation step and a subsequent alkoxylation step.

In practising the present process, the oxidation step is conducted by bringing the compound having the above-mentioned formula (II) into contact with an oxidizing agent in a suitable solvent. The solvent which may be employed in the reaction is of no particular limitation if it will not participate with the reaction and various inert organic solvents may be mentioned. As examples of such solvents may be mentioned, for instance, aromatic hydrocarbons such as benzene, toluene, halogenated hydrocarbons such as chloroform, methylene chloride; ethers such as dioxane, tetrahydrofuran and the like. The aromatic hydrocarbons such as benzene may be usually employed. The reaction may proceed with an oxidizing agent in a stoichiometric amount, but it is usually preferred for effecting rapid reaction to use an excess amount (about 1.5 – 10 times moles) of the oxidizing agent. The reaction temperature is not particularly critical, but the reaction may be usually effected at a temperature from room temperature to about 80° C. However, it is to be noted that the reaction may proceed at higher or lower temperatures. The time required for the reaction may be varied mainly upon the starting compound, the kind of the oxidizing agent, the sort of the solvent, the reaction temperature and the like, but it may usually take about 10 minutes to several hours. The compound having the above-mentioned formula (II) which may be employed in the process of this invention may be formed in situ by the interaction of an 7-aminocephalosporin or 6-aminopenicillin compound with an aryl aldehyde prior to the practice of the process of this invention and used per se in the present reaction.

The product formed by the oxidation may be recovered in a usual manner. For instance, the oxidizing agent is filtered off from the reaction mixture and the solvent is distilled off from the filtrate under reduced pressure to give the product. This product may be purified by a conventional method, e.g., column chromatography, but the product per se may be preferably employed without isolation and purification as a starting compound in the form of a solution in the subsequent step according to the process of this invention.

The alkoxylation step may be easily effected by contacting a solution of the aforesaid starting compound with a lower alkanol. The reaction may proceed in a stoichiometric amount of the alkanol, but an excess amount of the lower alkanol of about 10 – 100 times moles may be usually and preferably used for rapid reaction. The reaction temperature is not particularly critical and the reaction may be usually conducted at room temperature, but the reaction may proceed at higher or lower temperatures. As the reaction may be promoted with heating, the reaction may be, in some cases, effected with heating to about 40°–50° C. The time required for the reaction may be varied mainly upon the kind of the starting compound, the sort of the lower alkanol, the reaction temperature and the like, but it takes about 0.5– several hours.

The alkoxylated compound may be recovered from the reaction mixture in a usual manner. For instance, the solvent and excess alkanol are distilled off from the reaction mixture to give the amorphous end product in this step, which may be then purified by a conventional method, e.g., column chromatography.

The process of this invention may be more concretely illustrated by way of the examples and referential examples given below, but this invention is not to be limited by them.

EXAMPLE 1

2,2,2-Trichloroethyl 7α-methoxy-7β-(4-hydroxy-3,5-di-tert.-butylbenzylideneamino)-3-methyl-3-cephem-4-carboxylate Step A  2,2,2-Trichloroethyl 7β-(4-hydroxy-3,5-di-tert.-butylbenzylideneamino)-3-methyl-3-cephem-4-carboxylate To 10 g. of 2,2,2-trichloroethyl 7β-amino-3-methyl-3-cephem-4-carboxylate hydrochloride was added about 70 ml. of water. About 2.5 g. of sodium bicarbonate was added thereto and, after stirring for a while, the resultant was extracted with ethyl acetate. The extract was dried over anhydrous sodium sulfate and concentrated at a temperature below 35° C. The so obtained free base was dissolved in 40 ml. of methanol and 5 g. of 4-hydroxy-3,5-di-tert.-butylbenzaldehyde was added thereto and stirring was continued at room temperature for 4 hours. The insolubles were dissolved by heating briefly and the reaction mixture was concentrated into a half amount thereof, which was then cooled to separate out crystalline substances. The substances were recovered by filtration and washed with cold methanol to give 2,2,2-trichloroethyl 7β-(4-hydroxy-3,5-di-tert.-butylbenzylideneamino)-3-methyl-3-cephem-4-carboxylate. Yield 7 g. The product was recrystallized from a small amount of methanol to give the pure product as slightly yellow colored crystals. m.p. 94° C.

Analysis for $C_{25}H_{31}O_4N_2SCl_3$: Calculated: C, 53.43; H, 5.56; N, 4.99;  Found: C, 53.51; H, 5.61; N, 5.08

Step B  2,2,2-Trichloroethyl 7α-methoxy-7β-(4-hydroxy-3,5-di-tert.-butylbenzylideneamino)-3-methyl-3-cephem-4-carboxylate A mixture of 1 g. of 2,2,2-trichloroethyl 7β-(4-hydroxy-3,5-di-tert.-butyl-benzylideneamino)-3-methyl-3-cephem-4-carboxylate and 5 g. of lead dioxide in 75 ml. of benzene was refluxed with stirring for 15–20 minutes. After cooling, insolubles were filtered off and washed with benzene. The combined filtrate and washings were concentrated under reduced pressure to about 20 ml. and about 10 ml. of absolute methanol was added to the residue. After standing for 1 hour at room temperature, the reaction mixture was concentrated under reduced pressure to give the desired product. The product was purified by a column chromatography on dried silica gel (dried at 110° C. under reduced pressure for several hours) and elution with a solution system of cyclohexane-ethylacetate (3 : 1) to give 2,2,2-trichloroethyl 7α-methoxy-7β-(4-hydroxy-3,5-di-tert.-butylbenzylideneamino)-3-methyl-3-cephem-4-carboxylate as pale brown amorphous powders. Yield 700 mg.

The product has $M^+$ 590 in its mass spectrum.

NMR spectrum ($CDCl_3$) δ ppm:
 1.45 (C-($CH_3$)$_3$, singlet),
 2.21 ($CH_3$ at 3-position, singlet),
 3.35 ($H_2$ at 2-position, quartet),
 3.60 ($OCH_3$ at 7-position, singlet),
 4.90 ($CO_2CH_2CCl_3$, quartet),
 5.06 (H at 6-position, singlet),
 5.55 (OH at 4-position of benzene OH, singlet),
 7.65 (benzene H, singlet),
 8.55 (CH=N—, singlet), TLC (Thin-layer chromatography) (silica gel):
 Developing solvent, cyclohexane - ether (2 : 1)
 $R_f = 0.5$

EXAMPLE 2

Benzhydryl 7α-methoxy-7β-(4-hydroxy-3,5-di-tert.-butyl-benzylideneamino)-3-acetoxymethyl-3-cephem-4-carboxylate A mixture of 880 mg. of benzhydryl 7-aminocephalosporanate and 460 mg. of 4-hydroxy-3,5-di-tert.-butyl-benzaldehyde was refluxed in 50 ml. of benzene for 1.5 to 2 hours by the removal of water using a water separator to form the Schiff base in situ, which was used in subsequent reaction without any isolation procedures. To the reaction mixture was added 5 g. of lead dioxide and vigorous stirring was done for 15 minutes in an oil bath at 85° C. After cooling, the reaction mixture was filtered and 20 ml. of absolute methanol was added to the filtrate. After standing for 1 hour at room temperature, the reaction mixture was concentrated under reduced pressure to give a crude product. The product was purified by elution with a mixture of cyclohexane-ethyl acetate (3 : 1) on a column using about 50 g. of silica gel which was dried by heating under reduced pressure, thereby giving benzhydryl 7α-methoxy-7β-(4-hydroxy-3,5-di-tert.-butylbenzylideneamino)-3-acetoxymethyl-3-cephem-4-carboxylate. Yield 0.9 g.

NMR spectrum ($CDCl_3$) δ ppm:
 1.45 (C-($CH_3$)$_3$, singlet),
 1.98 ($CH_2OCOCH_3$ at 3-position, singlet),
 3.35 ($H_2$ at 2-position, quartet),
 3.55 ($OCH_3$ at 7-position $OCH_3$, singlet),
 4.80 ($CH_2OCOCH_3$ at 3-position, quartet),
 5.03 (H at 6-position, singlet),
 5.50 (OH at 4-position of benzene, singlet),
 6.07 (COOCH($C_6H_5$)$_2$, singlet),
 7.30 (COOCH ($C_6H_5$)$_2$, singlet),
 7.63 (H at 2,6-positions of benzene, singlet),
 8.45 (CH = N—, singlet), TLC (silica gel):
 Developing solvent, n-hexane-ethyl acetate (3 : 1)
 $R_f = 0.4$

EXAMPLE 3

Benzhydryl 7α-methoxy-7β-(4-hydroxy-3,5-di-tert.-butylbenzylideneamino)-3-(1-methyl-1H-tetrazol-5-yl)thiomethyl-3-cephem-4-carboxylate To 70 ml. of benzene were added 7.0 g of benzhydryl 7-amino-3-(1-methyl-1H-tetrazol-5-yl)-thiomethyl-3-cephem-4-carboxylate and 3.5 g. of 4-hydroxy-3,5-di-tert.-butylbenzaldehyde. The mixture was refluxed for 1.5 hours, while the water formed in situ during the reaction was removed by the use of a water separator. The resulting Schiff base solution was added to a mixture of 50 g. of lead dioxide and 300 ml. of benzene, which was pre-heated to 65° C under stirring. The resulting mixture was vigorously stirred at 65° C for 15 minutes. After cooling, the reaction mixture was filtered and to the filtrate was added 50 ml. of absolute methanol. The mixture was left standing at room temperature and then concentrated under reduced pressure to give the crude desired product. This product was purified by a column chromatography on dried silica gel, using a developing solvent of benzene-ethyl acetate (10 : 1) to give 4.65 g. of benzhydryl 7α-methoxy-7β-(4-hydroxy-3,5-di-tert.-butylbenzylideneamino)-3-(1-methyl-1H-tetrazol-5-yl)thiomethyl-3-cephem-4-carboxylate as pale reddish brown colored amorphous powders.

NMR spectrum (CDCl$_3$) δ ppm:
- 1.45 (C-(CH$_3$)$_3$, singlet),
- 3.58 (OCH$_3$ at 7-position, singlet),
- 3.61 (H$_2$ at 2-position, singlet),
- 3.79 (N—CH$_3$ in tetrazole at 3-position, singlet),
- 4.31 (—CH$_2$S— at 3-position, quartet),
- 5.09 (H at 6-position, singlet),
- 5.63 (OH at 4-position in benzene, singlet),
- 6.98 (COOC$\underline{H}$ (C$_6$H$_5$)$_2$, singlet),
- 7.38 (COOCH (C$_6\underline{H}_5$)$_2$, singlet),
- 7.72 (H at 2,6-positions in benzene, singlet),
- 8.60 (—CH=N—, singlet)

TLC (silica gel):
Developing solvent, benzene-ethyl acetate (10 : 1)
R$_f$ = 0.4

Following the substantially same procedures as above except that the reaction of the Schiff have and the lead dioxide was effected at a temperature of about 5°–10° C. under icecooling, there was obtained a similar result.

EXAMPLE 4

Benzhydryl 7α-methoxy-7β-(4-hydroxy-3-methyl-5-tert.-butylbenzylideneamino)-3-acetoxymethyl-3-cephem-4-carboxylate A mixture of 438 mg. of benzhydryl 7-aminocephalosporanate and 192 mg. of 4-hydroxy-3-methyl-5-tert-butylbenzaldehyde was refluxed for 1.5 hours in 15 ml. of benzene, while water is removed by a water separator to form the corresponding Schiff base. The reaction mixture was cooled and 1 g. of lead dioxide was added thereto. The mixture was vigorously stirred at room temperature for 30 minutes. The mixture was filtered and to the filtrate was added 4 ml. of absolute methanol and the solution was left standing at room temperature for 18 hours. The reaction mixture was concentrated under reduced pressure and the residue was purified by a column chromatography on silica gel, which was previously dried by heating under reduced pressure, by the use of a mixture of cyclohexane and ethyl acetate(3 : 1) as a developing solvent to give benzhydryl 7α-methoxy-7β-(4-hydroxy-3-methyl-5-tert-butylbenzylideneamino)-3-acetoxymethyl-3-cephem-4-carboxylate as pale yellow colored amorphous powders.
Yield 120 mg.

NMR spectrum (CDCl$_3$) δ ppm:
- 1.42 (C-(CH$_3$)$_3$, singlet),
- 1.98 (CH$_2$COOC$\underline{H}_3$ at 3-position, singlet),
- 2.23 (CH$_3$ at 3-position in benzene, singlet),
- 3.39 (H$_2$ at 2-position, quartet),
- 3.58 (OCH$_3$ at 7-position, singlet),
- 4.85 (C$\underline{H}_2$OCOCH$_3$ at 3-position, quartet),
- 5.07 (H at 6-position, singlet),
- 5.50 (OH at 4-position in benzene, singlet),
- 6.98 (COOC$\underline{H}$ (C$_6$H$_5$)$_2$, singlet),
- 7.37 (COOCH (C$_6\underline{H}_5$)$_2$, singlet),
- 7.59 (H at 2,6-positions in benzene, singlet),
- 8.53 (CH=N—, singlet), TLC (silica gel):
Developing solvent, cyclohexane-ethyl acetate (3 : 1)
R$_f$ = 0.40

EXAMPLE 5

Benzhydryl 7α-methoxy-7β-(4-hydroxy-3,5-dimethylbenzylideneamino)-3-acetoxymethyl-3-cephem-4-carboxylate Step A Benzhydryl 7β-(4-hydroxy-3,5-dimethylbenzylideneamino)-3-acetoxymethyl-3-cephem-4-carboxylate A mixture of 658 mg. of benzhydryl 7-aminocephalosporanate and 225 mg. of 4-hydroxy-3,5-dimethylbenzaldehyde were refluxed in 25 ml. of toluene for 2 hours, while water is removed by a water separator. After cooling, benzhydryl 7β-(4-hydroxy-3,5-dimethylbenzylideneamino)-3-acetoxymethyl-4-cephem-4-carboxylate was separated out in situ as colorless crystals, which were then recovered by filtration and washed with a small amount of toluene. Yield 690 mg. m.p. 187°–188° C (with decomp.)

Step B Benzhydryl 7α-methoxy-7β-(4-hydroxy-3,5-dimethylbenzylideneamino)-3-acetoxymethyl-3-cephem-4-carboxylate In 20 ml. of hot benzene was dissolved 300 mg. of benzhydryl 7β-(4-hydroxy-3,5-dimethylbenzylideneamino)-3-acetoxymethyl-3-cephem-4-carboxylate and 0.9 g of lead dioxide was added thereto. The mixture was stirred at room temperature for 30 minutes. The reaction mixture was filtered, to the filtrate was added 3 ml. of methanol and the mixture was left at room temperature for 18 hours. The reaction mixture was concentrated under reduced pressure. The residue was purified by a column chromatography using a mixture of cyclohexane and ethyl acetate (2 : 1) and silica gel, which was previously dried by heating under reduced pressure. By this purification was obtained benzhydryl 7α-methoxy-7β-(4-hydroxy-3,5-dimethylbenzylideneamino)-3-acetoxymethyl-3-cephem-4-carboxylate as pale yellow powders.
Yield 10 mg.

NMR spectrum (CDCl$_3$) δ ppm:
- 1.98 (OCOC$\underline{H}_3$ at 3-position, singlet),
- 2.25 (CH$_3$ at 3,5-positions in benzene, singlet),
- 3.38 (H$_2$ at 2-position, quartet),
- 3.56 (OCH$_3$ at 7-position, singlet),
- 4.93 (C$\underline{H}_2$OCOCH$_3$ at 3-position, quartet),
- 5,06 (H at 6-position, singlet),
- 6.98 (COOC$\underline{H}$ (C$_6$H$_5$)$_2$, singlet),
- 7.35 (COOCH (C$_6\underline{H}_5$)$_2$, singlet),
- 7.50 (H at 2,6-positions, singlet),
- 8.48 (CH=N—, singlet)

TLC (silica gel):
Developing solvent, cyclohexane-ethyl acetate (2 : 1)
R$_f$ = 0.4

EXAMPLE 6 benzhydryl 7α-ethoxy-7β-(4-hydroxy-3,5-di-tert.-butylbenzylideneamino)-3-acetoxymethyl-3-cephem-4-carboxylate In 50 ml. of benzene was dissolved 2 g. of benzhydryl 3-acetoxymethyl-7-(4-hydroxy-3,5-di-tert.-butylbenzylideneamino)-3-cephem-4-carboxylate and 5 g. of lead dioxide was added thereto. Heating with stirring was done for 15 minutes. After cooling the reaction mixture was filtered and to the filtrate was added 20 ml. of ethanol. The resulting mixture was left at room temperature for 1.5 hours. The reaction mixture was concentrated at room temperature and the residue was purified by a column chromatography on dried silica gel, using a developing solvent of cyclohexane and ethyl acetate (3 : 1) to give 700 mg. of benzhydryl 7α-ethoxy-7β-(4-hydroxy-3,5-di-tert.-butylbenzylideneamino)-3-acetoxymethyl-3-cephem-4-carboxylate as reddish orange colored powders.

NMR spectrum (CDCl$_3$) δ ppm:
1.22 (OCH$_2$CH$_3$ at 7-position, triplet), 1,45 (C·(CH$_3$)$_3$, singlet),
2.00 (CH$_2$OCOCH$_3$ at 3-position, singlet),
3.41 (H$_2$ at 2-position, doublet),
3.83 (OCH$_2$CH$_3$ at 7-position, quartet),
4.90 (—CH$_2$OAc at 3-position, quartet),
5.05 (H at 6-position, singlet),
5.62 (phenolic OH, singlet),
6.98 (COOCH (C$_6$H$_5$)$_2$, singlet),
7.38 (COOCH (C$_6$H$_5$)$_2$, singlet),
7.72 (H at 2,6-positions in benzene nucleus, singlet),
8.56 (C=N—, singlet).

EXAMPLE 7

Benzhydryl 7α-methoxy-7β-(4-hydroxy-3,5-diisopropylbenzylideneamino)-3-acetoxymethyl-3-cephem-4-carboxylate In 15 ml. of benzene was dissolved 500 mg. of benzhydryl-7-(4-hydroxy-3,5-diisopropylbenzylideneamino)-3-acetoxymethyl-3-cephem-4-carboxylte and 1 g. of PbO$_2$ (lead dioxide) which was freshly prepared, was added thereto. The resulting mixture was stirred at room temperature for 20 minutes. Insolubles were filtered off, to the filtrate was added 4 ml. of methanol and then the mixture was left at room temperature overnight. The reaction mixture was concentrated under reduced pressure to give the desired product. The product was purified by a column chromatography on dried silica gel (dried at 110° C. under reduced pressure for several hours), using as a developing solvent a mixture of cyclohexane-ethyl acetate (3 : 1) to give benzhydryl 7α-methoxy-7β-(4-hydroxy-3,5-diisopropylbenzylideneamino)-3-acetoxymethyl-3-cephem-4-carboxylate as pale yellow colored amorphous powders.
Yield 202 mg.

NMR spectrum (CDCl$_3$) δ ppm:
1.30 (CH·(CH$_3$)$_2$, doublet),
2.00 (CH$_2$OCOCH$_3$ at 3-position, singlet),
3.14 (CH (CH$_3$)$_2$, multiplet),
3.42 (H$_2$ at 2-position, quartet),
3.61 (OCH$_3$ at 7-position, singlet),
4.88 (CH$_2$OCOCH$_3$ at 3-position, quartet),
5.13 (H at 6-position, singlet),
7.03 (COOCH (C$_6$H$_5$)$_2$, singlet),
7.41 (COOCH (C$_6$H$_5$)$_2$, singlet),
7.61 (H at 2,6-positions of benzene, singlet), 8.60 (CH=N—, singlet)
TLC (silica gel):
Developing solvent, cyclohexane-ethyl acetate (3 : 1)
R$_f$ = 0.3

EXAMPLE 8

Benzhydryl 7α-methoxy-7β-(4-hydroxy-3,5-di-tert.-butylbenzylideneamino)-3-(2-(5-methyl-1,3,4-thiadiazolyl)-thiomethyl)-3-cephem-4-carboxylate In 10 ml. of benzene was dissolved 300 mg. of benzhydryl 7β-(4-hydroxy-3,5-di-tert.-butylbenzylideneamino)-3-(2-(5-methyl-1,3,4-thiadiazolyl)thiomethyl)-3-cephem-4-carboxylate and 600 mg. of lead dioxide was added thereto. The mixture was stirred at room temperature for 30 minutes. The reaction mixture was filtered and to the filtrate was added 4 ml. of methanol followed by standing at room temperature for 1 hour. The reaction mixture was concentrated and the residue was purified by a column chromatography on dried silica gel, using a developing solvent of cyclohexane-ethyl acetate (2 : 1) to give 180 mg. of benzhydryl 7α-methoxy-7β-(4-hydroxy-3,5-di-tert.-butylbenzylideneamino)-3-(2-(5-methyl-1,3,4-thiadiazolyl)-thiomethyl)-3-cephem-4-carboxylate as pale yellow colored powders.

NMR spectrum (CDCl$_3$) δ ppm:
1.44 (C·(CH$_3$)$_3$, singlet),
2.66 (CH$_3$ at 5-position in thiadiazole on 3-position, singlet),
3.57 (H$_2$ at 2-position and OCH$_3$ at 7-position, singlet),
4.32 (—CH$_2$S— at 3-position, quartet),
5.06 (H at 6-position, singlet),
5.60 (phenolic OH, singlet),
6.95 (COOCH (C$_6$H$_5$)$_2$, singlet),
7.33 (COOCH (C$_6$H$_5$)$_2$, singlet),
7.66 (H at 2,6-positions of benzene nucleus, singlet),
8.53 (CH = N—, singlet).
TLC (silica gel):
Developing solvent, cyclohexane-ethyl acetate (2 : 1)
R$_f$ = 0.4

EXAMPLE 9 p-Toluenesulfonylethyl 7α-methoxy-7β-(4-hydroxy-3,5-di-tert.-butylbenzylideneamino)-3-methyl-3-cephem-4-carboxylate In 40 ml. of benzene was dissolved 1.0 g. of p-toluenesulfonylethyl 7β-(4-hydroxy-3,5-di-tert.-butylbenzylideneamino)-3-methyl-3-cephem-4-carboxylate and 2 g. of lead dioxide was added thereto. The mixture was stirred at room temperature for 30 minutes. The reaction mixture was filtered, the filtrate was concentrated under reduced pressure to a half amount thereof, 20 ml. of methanol was added thereto and the mixture was left at room temperature overnight. The reaction mixture was concentrated and the residue was purified by a column chromatography on dried silica gel, using eluants of cyclohexane-ethyl acetate (10 : 1 and 5 : 1) to give 0.45 g. of p-toluenesulfonylethyl 7α-methoxy-7β-(4-hydroxy-3,5-di-tert.-butylbenzylideneamino)-3-methyl-3-cephem-4-carboxylate as powders.

NMR spectrum (CDCl$_3$) δ ppm:
1.41 (C·(CH$_3$)$_3$, singlet),
2.00 (CH$_3$ at 3-position, singlet),
2.40 (C$_6$H$_4$·CH$_3$ in ester, singlet),
3.21 (H$_2$ at 2-position, quartet),
3.53 (COOCH$_2$CH$_2$SO$_2$ in ester, triplet),
3.54 (OCH$_3$ at 7-position, singlet),
4.55 (COOCH$_2$CH$_2$SO$_2$ in ester, triplet),
4.96 (H at 6-position, singlet),
5.59 (phenolic OH, singlet), 7.59 (SO$_2$—C$_6$H$_4$—CH$_3$ in ester, quartet),
7.63 (H at 2,6-positions in benzene nucleus, singlet),
8.44 (CH = N—, singlet)
TLC (silica gel):
Developing solvent, cyclohexane-ethyl acetate (5: 1)
R$_f$ = 0.5

EXAMPLE 10

Benzhydryl 7α-methoxy-7β-(4-hydroxy-3,5-di-tert.-butylbenzylideneamino)-3-acetoxymethyl-3-cephem-4-carboxylate To 350 mg. of benzhydryl 7β-(4-hydroxy-3,5-di-tert.-butylbenzylideneamino)-3-acetoxymethyl-3-cephem-4-carboxylate was added a solution of 113.5 mg. of 2,3-dichloro-5,6-dicyanobenzoquinone in 8.6 ml. of benzene and the resulting mixture was stirred at room temperature for 30 minutes. The reaction mixture was concentrated and the residue was extracted with a mixture of cyclohexane-ethyl acetate (5 : 1). The extract was concentrated, the concentrate was again disolved in 5 ml. of benzene, 4 ml. of methanol was added thereto and the mixture was left standing at room temperature for 30 minutes. Then, the reaction mixture was concentrated under reduced pressure to give the crude product. This product was purified by a dry silica gel column chromatography eluting with cyclohxane-ethyl acetate (3 : 1) to give benzhydryl 7α-methoxy-7β-(4-hydroxy-3,5-di-tert.-butylbenzylideneamino)-3-acetoxymethyl-3-cephem-4-carboxylate. Yield 156 mg.

The NMR spectrum and thin-layer chromatography of this product coincided with those shown in Example 2.

EXAMPLE 11

Benzhydryl 7α-methoxy-7β-(4-hydroxy-3,5-di-tert.-butylbenzylideneamino)-3-acetoxymethyl-3-cephem-4-carboxylate In 8.6 ml. of methanol were dissolved 330 mg. of benzhydryl 7β-(4-hydroxy-3,5-di-tert.-butylbenzylideneamino)-3-acetoxymethyl-3-cephem-4-carboxylate and 113.5 mg. of 2,3-dichloro-5,6-dicyanobenzoquinone and the resulting solution was stirred in an ice bath for 10 minutes. The reaction mixture was concentrated and the concentrate was extracted with benzene. The benzene extract was concentrated and the residue was chromatographed on a dry silica gel column with cyclohexane-ethyl acetate (3 : 1) as eluant to give benzhydryl 7α-methoxy-7β-(4-hydroxy-3,5-di-tert.-butylbenzylideneamino)-3-acetoxymethyl-3-cephem-4-carboxylate as amorphous powders.
Yield 161 mg.

The NMR spectrum and thin-layer chromatography of this product coincided with those shown in Example 2.

EXAMPLE 12

2,2,2-Trichloroethyl 7α-methoxy-7β-(4-hydroxy-3,5-di-tert.-butylbenzylideneamino)-3-methyl-3-cephem-4-carboxylate In 7.6 ml. of methanol were dissolved 281 mg. of the 7β-(4-hydroxy-3,5-di-tert.-butylbenzylideneamine)-3-methyl-3-cephem-4-carboxylate obtained in step A of Example 1 and 113.5 mg. of 2,3-dichloro-5,6-dicyanobenzoquinone and the resulting solution was stirred in an ice bath for 10 minutes. The reaction mixture was concentrated and the concentrate was extracted with benzene. The benzene extract was concentrated and the residue was chromatographed on a dry silicon gel column with cyclohexane-ethyl acetate (3 : 1) to give 2,2,2-trichloroethyl 7α-methoxy-7β-(4-hydroxy-3,5-di-tert.-butylbenzylideneamino)-3-methyl-3-cephem-4-carboxylate as amorphous powders. Yield 162 mg.

The NMR spectrum and thin-layer chromatography of this product coincided with those shown in step B of Example 1.

EXAMPLE 13

Benzhydryl 7α-methoxy-7β-(4-hydroxy-3-tert.-butyl-1-naphthylmethyleneamino)-3-acetoxymethyl-3-cephem-4-carboxylate In 25 ml. of benzene was dissolved 1.0 g. of benzhydryl 7β-(4-hydroxy-3-tert.-butyl-1-naphthylmethyleneamino)-3-acetoxymethyl-3-cephem-4-carboxylate, 2 g. of lead dioxide was added thereto with stirring in an ice-water bath and the mixture was stirred for 20 minutes in an ice-water bath. Insolubles were filtered off, 10 ml. of methanol was added to the filtrate, and, after standing at room temperature overnight, the reaction mixture was concentrated under reduced pressure to give the desired product. The product was purified by a column chromatography on dry silica gel developed with benzene - ethyl acetate (10 : 1) to give benzhydryl 7α-methoxy-7β-(4-hydroxy-3-tert.-butyl-1-naphthylmethyleneamino)-3-acetoxymethyl-3-cephem-4-carboxylate as powders. Yield 536 mg.

NMR spectrum (CDCl$_3$) δ ppm:
1.43 (C·(CH$_3$)$_3$, singlet),
1.93 (CH$_2$OCC$\underline{CH_3}$ at 3-position, singlet),
3.32 (H$_2$ at 2-position, quartet),
3.56 (OCH$_3$ at 7-position, singlet),
5.06 (H at 6-position, singlet),
6.93 (COOC$\underline{H}$(C$_6$H$_5$)$_2$, singlet),
7.28 (COOC$\underline{H}$ (C$_6$H$_5$)$_2$, multiplet)
TLC (silica gel):
Developing solvent, benzene-ethyl acetate (10 : 1)
R$_f$ = 0.4

EXAMPLE 14

Benzhydryl 7α-methoxy-7β-(4-hydroxy-3-tert.-butyl-5,6,7,8-tetrahydro-1-naphthylmethyleneamino)-3-acetoxymethyl-3-cephem-4-carboxylate In 10 ml. of 1,2-dichloroethane was dissolved 260 mg. of benzhydryl 7β-(4-hydroxy-3-tert.-butyl-5,6,7,8-tetrahydro-1-naphthylmethyleneamino)-3-acetoxymethyl-3-cephem-4-carboxylate, 520 mg. of load dioxide was added thereto with stirring in an ice-water bath and the mixture was stirred for 20 minutes in an ice-water bath. Insolubles were filtered off, 5 ml. of methanol was added to the filtrate and, after standing at room temperature for 1.5 hours, the reaction mixture was concentrated under reduced pressure to give the desired product. The product was purified by a column chromatography on dried silica gel developed with benzene - ethyl acetate (30 : 1) to give benzhydryl 7α-methoxy-7β-(4-hydroxy-3-tert.-butyl-5,6,7,8-tetrahydro-1-naphthylmethyleneamino)-3-acetoxymethyl-3-cephem-4-carboxylate as powders. Yield 155 mg.

NMR spectrum (CDCl$_3$) δ ppm:
1.33 (C·(CH$_3$)$_3$, singlet), 1.70 (H$_2$ at 6,7-positions in 5,6,7,8-tetrahydronaphthylmethylene nucleus, broad singlet),
1.90 (CH$_2$COOCH$_3$ at 3-position, singlet),
2.70 (H$_2$ at 5,8-positions in 5,6,7,8-tetrahydronaphthylmethylene nucleus, broad doublet),
3.40 (H$_2$ at 2-position, quartet),
3.48 (CCH$_3$ at 7-position, singlet),
4.79 (CH$_2$OCOCH$_3$ at 3-position, quartet),
4.96 (H at 6-position, singlet),
6.84 (COOCH (C$_6$H$_5$)$_2$, singlet),
7.23 (COOCH (C$_6$H$_5$)$_2$, broad singlet),
7.67 (H at 2-position in 5,6,7,8-tetrahydronaphthylmethylene nucleus, singlet).
8.70 (CH:N—, singlet)

TLC (silica gel):
Developing solvent, benzene-ethyl acetate (10 : 1)
R$_f$ = 0.5

EXAMPLE 15 p-Bromophenacyl 7α-methoxy-7β-(4-hydroxy-3,5-di-tert.-butylbenzylideneamino)-3-acetoxymethyl-3-cephem-4-carboxylate In 30 ml. of 1,2-dichloroethane was dissolved 1.0 g. of p-bromophenacyl 7β-(4-hydroxy-3,5-di-tert.-butylbenzylideneamino)-3-acetoxymethyl-3-cephem-4-carboxylate and 2.0 g. of lead dioxide was added thereto when an inner temperature reached −5° C. with stirring in an ice-salt bath. Then, the mixture was stirred, maintaining the temperature at 0° − −5° C. for 30 minutes. Insolubles were filtered off, 10 ml. of methanol was added to the filtrate and the mixture was left at room temperature overnight. The reaction mixture was concentrated under reduced pressure to give the desired product. The compound was purified by a column chromatography on dried silica gel developed with benzene - ethyl acetate (10 : 1) to give p-bromophenacyl 7α-methoxy-7β-(4-hydroxy-3,5-di-tert.-butylbenzylideneamino)-3-acetoxymethyl-3-cephem-4-carboxylate as powders. Yield 628 mg.

NMR spectrum (CDCl$_3$) δ ppm:
1.46 (C·(CH$_3$)$_3$, singlet),
2.06 (CH$_2$COOCH$_3$ at 3-position, singlet),
3.43 (H$_2$ at 2-position, quartet),
3.54 (OCH$_3$ at 7-position, singlet),
4.99 (CH$_2$OCOCH$_3$ at 3-position, broad singlet),
5.08 (H at 6-position, singlet),
5.49 (COOCH$_2$COC$_6$H$_4$Br, quartet),
5.61 (phenolic OH, singlet),
7.67 (H at 2,6-positions in benzene nucleus, singlet),
7.72 (COOCH$_2$CO C$_6$H$_4$Br, quartet),
8.52 (CH=N—, singlet)

TLC (silica gel):
Developing solvent, benzene-ethyl acetate (10 : 1)
R$_f$ = 0.5

EXAMPLE 16 p-Bromophenacyl 7α-methoxy-7β-(4-hydroxy-3,5-di-tert.-butylbenzylidenamino)-3-(1-methyl-1H-tetrazol-5-yl)-thiomethyl-3-cephem-4-carboxylate In 20 ml. of tetrahydrofuran was dissolved 724 mg. of p-bromophenacyl 7β-(4-hydroxy-3,5-di-tert.-butylbenzylidenamino)-3-(1-methyl-1H-tetrazol-5-yl)thiomethyl-3-cephem-4-carboxylate, 1.6 g. of lead dioxide was added thereto with stirring in an ice-water bath and the mixture was stirred for 30 minutes in an ice-water bath. Insolubles were filtered off, 10 ml. of methanol was added to the filtrate and, after standing at room temperature for 1 hour, the reaction mixture was concentrated under reduced pressure to give the desired product. The product was purified by a column chromatography on dried silica gel developed with benzene - ethyl acetate (10 : 1) to give p-bromophenacyl 7α-methoxy-7β-(4-hydroxy-3,5-di-tert.-butylbenzylideneamino)-3-(1-methyl-1H-tetrazol-5-yl)-thiomethyl-3-cephem-4-carboxylate as pale yellow powders. Yield 512 mg.

NMR spectrum (CDCl$_3$) δ ppm:
1.39 (C·(CH$_3$)$_3$, singlet),
3.48 (OCH$_3$ at 7-position, singlet),
3.61 (H$_2$ at 2-position, singlet),
3.81 (N-CH$_3$ in tetrazole at 3-position, singlet),
4.38 (—CH$_2$S— at 3-position, singlet),
5.03 (H at 6-position, singlet),
5.45 (COOCH$_2$ COC$_6$H$_4$Br, singlet),
5.55 (phenolic OH, singlet),
7.61 (H at 2,6-positions in benzene nucleus, singlet),
7.66 (COOCH$_2$ COC$_6$H$_4$Br, quartet),
8.46 (—CH=N—, singlet)

TLC (silica gel):
Developing solvent, benzene-ethyl acetate (10 : 1)
R$_f$ = 0.3

EXAMPLE 17

2,2,2-Trichloroethyl 6β-(3,5-di-tert.-butyl-4-hydroxybenzylideneamino)-6α-methoxypenicillanate To 1.89 g. of 2,2,2-trichloroethyl 6-(3,5-di-tert.-butyl-4-hydroxybenzylideneamino)-penicillanate in 40 ml. of benzene was added 3.8 g. of lead dioxide. After stirring at room temperature for 20 minutes, insolubles were filtered off, and then the filtrate was concentrated at room temperature to about one-half of its original volume. To this concentrate was added 15 ml. of methanol, and, after standing at room temperature for one hour, the solvent was distilled off. The residue thus obtained was purified by a dry silica gel column chromatography (3 × 36 cm, eluent; ethyl acetate - cyclohexane, 1 : 10) to give 725 mg. of 2,2,2-trichloroethyl 6β-(3,5-di-tert.-butyl-4-hydroxybenzylideneamino)-6α-methoxypenicillanate as a pale yellow powder.

IR spectrum $\nu_{max}^{nujol}$ cm$^{-1}$ : 3650, 1770, 1690, 1635
NMR spectrum δ ppm (CDCl$_3$)
8.47 (1H, singlet, 6-position CH=N)
7.66 (2H, singlet, benzene ring H)
5.59 (1H, singlet, 5-position H)
4.78 (2H, singlet, CH$_2$CCl$_3$)
4.55 (1H, singlet, 3-position H)
3.55 (3H, singlet, 6-position OCH$_3$)
1.66 (3H, singlet, 2-position CH$_3$)
1.53 (3H, singlet, 2-position CH$_3$)
1.43 (18H, singlet, t-butyl)

EXAMPLE 18

Pivalcyloxymethyl 6β-(3,5-di-tert.-butyl-4-hydroxybenzylideneamino)-6α-methoxypenicillanate Following the same procedure as described in Example 17, there was obtained 750 mg. of pivaloyloxymethyl 6β-(3,5-di-tert.-butyl-4-hydroxybenzylideneamino)-6α-methoxypenicillanate from 1.89 g. of pivaloyloxymethyl 6β-(3,5-di-tert.-butyl-4-hydroxybenzylideneamino)-penicillanate.

IR spectrum $\nu_{max}^{CHCl_3}$ cm$^{-1}$: 3630, 1760, 1630
NME spectrum δ ppm (CDCl$_3$)
- 8.45 (1H, singlet, 6-position CH=N)
- 7.64 (2H, singlet, benzene ring H) 5.84 (2H, singlet, COOCH$_2$O—)
- 5.58 (1H, singlet, benzene ring H)
- 5.53 (1H, singlet, 5-position H)
- 4.45 (1H, singlet, 3-position H)
- 3.55 (3H, singlet, 6-position OCH$_3$)
- 1.60 (3H, singlet, 2-position CH$_3$)
- 1.45 (21H, singlet, 2-position CH$_3$ and benzene ring t-butyl)
- 1.22 (9H, singlet, pivaloyl)

EXAMPLE 19

Benzhydryl 6β-(3,5-di-tert.-butyl-4-hydroxybenzylideneamino)-6α-metoxypenicillanate Following the same procedures as described in Example 17, there was obtained 400 mg. of benzhydryl 6β-(3,5-di-tert.-butyl-4-hydroxybenzylideneamino)-6α-methoxypenicillanate from 1.89 g. of benzhydryl 6β-(3,5-di-tert.-butyl-4-hydroxybenzylideneamino)penicillanate.

IR spectrum $\nu_{max}^{nujol}$ cm$^{-1}$: 3640, 1770, 1750, 1630
NMR spectrum δ ppm (CDCl$_3$)
- 8.42 (1H, singlet, 6-position CH=H).
- 7.60 (2H, singlet, 6-position benzene ring H)
- 7.25 (10H, singlet, benzhydrylester benzene ring H)
- 6.87 (1H, singlet, COOCH φ$_2$)
- 3.51 (2H, singlet, benzene ring OH and 5-position H)
- 4.44 (1H, singlet, 3-position H)
- 3.46 (3H, singlet, 6-position OCH$_3$)
- 1.53 (3H, singlet, 2-position CH$_3$)
- 1.38 (21H, singlet, 2-position CH$_3$ and t-butyl)

EXAMPLE 20

2,2,2-Trichloroethyl 7β-(3,5-di-tert.-butyl-4-hydroxybenzylideneamino)-7α-methoxy-3-methyl-2-cephem-4-carboxylate To a solution of 1.45 g. of 2,2,2-trichloroethyl 7β-(3,5-di-tert.-butyl-4-hydroxybenzylideneamino)-3-methyl-2-cephem-4-carboxylate in 50 ml. of benzene was added 2.5 g. of lead dioxide, and the resulting mixture was stirred at room temperature for 25 minutes. Insolubles were filtered off, and 20 ml. of methanol was added to the filtrate. Then, the mixture was allowed to stand at room temperature for 2 hours. The reaction mixture was concentrated, and the residue was purified by a dry silica gel column chromatography (3 × 25 cm, eluent; ethyl acetate-cyclohexane, 1 : 5) to give 126 mg. of 2,2,2-trichloroethyl 7β-(3,5-di-tert.-butyl-4-hydroxybenzylideneamino)-7α-methoxy-3-methyl-2-cephem-4-carboxylate.

NMR spectrum δ ppm (CDCl$_3$)
- 8.46 (1H, singlet, 7-position CH=N)
- 7.66 (2H, singlet, benzene ring H)
- 5.91 (1H, broad, 2-position H)
- 5.59 (1H, broad, benzene ring H)
- 5.36 (1H, singlet, 6-position H)
- 4.91 (1H, broad, 4-position H)
- 4.78 (2H, doublet, CH$_2$CCl$_3$)
- 3.53 (3H, singlet, 7-position OCH$_3$)
- 1.93 (3H, singlet, 3-position CH$_3$)
- 1.44 (18H, singlet, t-butyl)

Following the same procedure as described above except for employing the corresponding benzhydrylester in place of the 2,2,2-trichloroethylester, there was obtained benzhydryl 7β-(3,5-di-tert.-butyl-4-hydroxybenzylideneamino)-7α-methoxy-3-methyl-2-cephem-4-carboxylate, yield 21.8%.

IR spectrum $\nu_{max}^{CHCl_3}$ cm$^{-1}$: 3650, 1765, 1745, 1690, 1660, 1630
NMR spectrum δ ppm (CDCl$_3$)
- 8.42 (1H, singlet, CH=N)
- 7.60 (2H, singlet, 7-position benzene ring H)
- 7.24 (10H, singlet, COOCH Ph$_2$)
- 6.83 (1H, singlet, COOCH Ph$_2$)
- 5.83 (1H, broad, 2-position H)
- 5.54 (1H, singlet, benzene ring H)
- 5.26 (1H, singlet, 6-position H)
- 4.81 (1H, broad, 4-position H)
- 3.45 (3H, singlet, 7-position OCH$_3$)
- 1.73 (3H, singlet, 2-position CH$_3$)
- 1.38 (18H, singlet, t-butyl)

EXAMPLE 21

Benzhydryl 3-acetoxymethyl-7β-(3,5di-tert.-butyl-4-hydroxybenzylideneamino)-7α-methoxy-2-cephem-4-carboxylate Following the same procedures as described in Example 20, benzhydryl 3-acetoxymethyl-7β-(3,5-di-tert.-butyl-4-hydroxybenzylideneamino)-7α-methoxy-2-cephem-4-carboxylate was obtained from benzhydryl 3-acetoxymethyl-7β-(3,5-di-tert.-butyl-4-hydroxybenzylideneamino)-2-cephem-4-carboxylate, yield 24.6%.

IR spectrum $\nu_{max}^{CHCl_3}$ cm$^{-1}$: 3650, 1770, 1745, 1635
NMR spectrum δ ppm (CDCl$_3$)
- 8.43 (1H, singlet, CH=N)
- 7.62 (2H, singlet, 7-position benzene ring H)
- 7.24 (10H, singlet, COOCH Ph$_2$)
- 6.83 (1H, singlet, COOCH Ph$_2$)
- 6.26 (1H, broad, 2-position H)
- 5.51 (1H, singlet, benzene ring OH)
- 5.17 (1H, singlet, 6-position H)
- 5.08 (1H, broad, 4-position H)
- 4.47 (2H, singlet, 3-position —CH$_2$O—)
- 3.39 (3H, singlet, 7-position OCH$_3$)
- 1.85 (3H, singlet, OOOCH$_3$)
- 1.37 (18H, singlet, t-butyl)

REFERENTIAL EXAMPLE 1

In 5 ml. of dichloroethane was dissolved 200 mg. of the benzhydryl 7α-methoxy-7β-(4-hydroxy-3,5-di-tert.-butylbenzylideneamino)-3-acetoxymethyl-3-cephem-4-carboxylate obtained in Example 2 and 100 mg. of thienylacetic chloride was added thereto. Stirring was effected at room temperature for 2 hours. The reaction mixture was purified on a thin-layer chromatography (silica gel; 20 × 20 cm, a thickness of 0.2 cm; developing solvent ethyl acetate-benzene (1 : 4)), the substance existing in the neighbourhood of R$_f$0.45 was extracted with ethyl acetate. The extract was concentrated under reduced pressure to give 60 mg. of benzhydryl 3-acetoxymethyl-7α-methoxy-7β-(2-thienylacetamido)-3-cephem-4-carboxylate.

NMR spectrum (CDCl$_3$) δ ppm:
- 2.0 (3-position OCOCH$_3$, singlet),
- 3.30 and 3.45 (2-position H$_2$, AB type),
- 3.48 (7-position OCH$_3$, singlet),

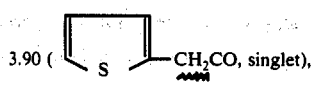

3.90 (   , CH₂CO, singlet), 4.90 and 5.05 (3-position-CH₂OCOCH₃, AB Type)
5.08 (6-position H, singlet),
6.9 – 7.5 (thiophene H, multiplet),
7.05 (COOCH (C₆H₅)₂, singlet),
7.35 (COOCH (C₆H₅)₂, singlet)

The benzhydrylester is hydrolyzed with trifluoroacetic acid in amisole in a usual manner to give 3-acetoxymethyl-7α-methoxy-7β-(2-thienylacetamido)-3-cephem-4-carboxylic acid.

REFERENTIAL EXAMPLE 2

2,2,2-Trichloroethyl
6β-(3,5-di-tert.-butyl-4-hydroxybenzylideneamino)-penicillante A mixture of 1 g. of 2,2,2-trichloroethyl 6β-aminopenicillanate and 674 mg. of 3,5di-tert.-butyl-4-hydroxybenzaldehyde in 40 ml. of benzene was refluxed for 1 hour in a vessel equipped with a water separator. The reaction mixture was concentrated, and the residue was dissolved in a small amount of a mixture of ethyl acetate and cyclohexane (1 : 10). Insolubles were filtered off, and the filtrate was purified by a dry silica gel column chromatography (3 × 32 cm, eluent; ethyl acetate - cyclohexane, 1 : 10) to give 1.11 g. of the desired product as a pale yellow syrup.

NMR spectrum δ ppm (CDCl₃)
8.46 (1H, doublet, J=2, CH=N),
7.56 (2H, singlet, benzene ring H),
5.61 (1H, doublet, J=4, 5-position H),
5.50 (1H, broad, CH),
5.33 (1H, quartet, J=2 and 4, 6-position H),
4.85 and 4.65 (each, 1H, doublet, J=12, CH₂CCl₃),
4.47 (1H, singlet, 3-position),
1.69 and 1.53 (each, 3H, singlet, 2-position CH₃),
1.39 (18H, singlet, t-butyl)

The pivaloyloxymethylester and the benzhydrylester were obtained in the same manner as above.

REFERENTIAL EXAMPLE 3

2,2,2-Trichloroethyl
7β-(3,5-di-tert.-butyl-4-hydroxybenzylideneamino)-3-methyl-2-cephem-4-carboxylate A solution of 2.14 g. of 2,2,2-trichloroethyl 7β-amino-3-methyl-2-cephem-4-carboxylate and 1.3 g. of 3,5-di-tert.-butyl-4-hydroxybenzaldehyde in 60 ml. of benzene was refluxed for 1.5 hours in a vessel equipped with a water separator. After evaporation of the solvent, a small amount of cyclohexane was added to the residue. Insolubles were filtered off, and the filtrate was purified by a dry silica gel column chromatography (4.5 × 15 cm, eluent; ethyl acetate-cyclohexane, 1 : 10) to give the desired product.
Yield 1.84 g.

NMR spectrum δ ppm (CDCl₃)
8.53 (1H, doublet, J=2, CH=N),
7.60 (2H, singlet, benzene ring H),
6.04 (1H, broad, 2-position H),
5.53 (1H, broad, OH),
5.45 (2H, multiplet, 6- and 7-positions H),
4.88 (1H, broad, 4-position H),
4.79 (2H, doublet, CH₂CCl₃), 1.93 (3H, singlet, 3-position CH₃)
1.44 (18H, singlet, t-butyl)

The benzhydrylester was obtained in the same manner as above.

What is claimed is:
1. A process for preparing a compound having the formula

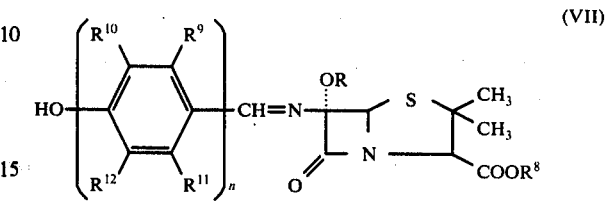

(VII)

wherein $R^8$ represents a group selected from the group consisting of straight or branched lower alkyl, lower alkoxymethyl, benzyloxymethyl, lower alkanoyloxy lower alkyl, benzoyloxymethyl, cyanomethyl, 2,2,2-trichloroethyl, phthalimidomethyl, benzyl, p-methoxybenzyl, p-nitrobenzyl, benzhydryl, phenacyl, p-bromophenacyl, p-methoxyphenacyl, p-nitrophenacyl, and tri lower alkylsilyl, $R^9$ to $R^{12}$ may be the same or different and each represents hydrogen or a group selected from the group consisting of straight or branched lower alkyl, lower alkoxy, halogen, cyano, lower alkoxycarbonyl, or $R^9$ and $R^{10}$ together and $R^{11}$ and $R^{12}$ together may be linked to form a ring fused with the benzene ring to which they are attached, n is 1 or 2 and R represents a straight or branched alkyl having from 1 to 6 carbon atoms which comprises contacting a penam compound having the formula

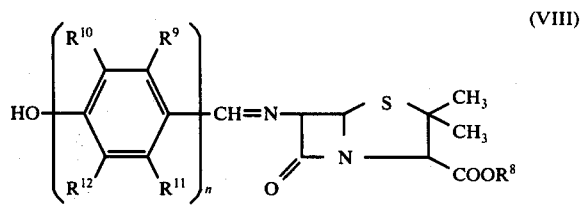

(VIII)

wherein $R^8$ to $R^{12}$ and n have the same meanings as defined above, with a metal oxide in an inert solvent or with a quinone compound substituted with an electron attractive group thereby oxidizing said panam compound to its quinoid form, and contacting the resulting oxidation product with a lower alkanol having the formula R—OH wherein R has the same meaning as defined above, said metal oxide and said quinone compound being one which oxidizes phenol to a quinoid form without destruction of the penam nucleus.

2. A process according to claim 1 wherein said metal oxide is lead dioxide and said inert solvent is benzene.

3. The process according to claim 1, wherein said quinone compound is dichlorodicyanobenzoquinone.

4. The process according to claim 1, wherein the metal oxide is lead dioxide, said solvent is benzene and said lower alkanol is methanol.

5. The process according to claim 1, wherein $R^9$ and $R^{11}$ are each hydrogen, $R^{10}$ and $R^{12}$ are each tertiary butyl, and R is methyl.

6. The process according to claim 5, wherein the metal oxide is lead dioxide and the solvent is benzene.

7. The process according to claim 5, wherein the said quinone compound is dichlorodicyanobenzoquinone.

8. The process according to claim 1, wherein the penam compound is so contracted at a temperature of up to about 80° C.

9. The process according to claim 1, wherein the alkanol is used in an excess of the stoichiometric amount related to the amount of the oxidation product.

10. The process according to claim 1, wherein the resulting oxidation product is so contacted at a temperature of from about 40° C. to about 50° C.

* * * * *

UNITED STATES PATENT AND TRADEMARK OFFICE
CERTIFICATE OF CORRECTION

PATENT NO. : 4,071,681
DATED : January 31, 1978
INVENTOR(S) : HIROAKI YANAGISAWA et al Page 1 of 3

It is certified that error appears in the above-identified patent and that said Letters Patent are hereby corrected as shown below:

Column 7, line 1: replace "limidazolinylthiomethyl" with ---1-imidazolinylthiomethyl---.

Column 10, line 35: replace "6.07" with ---6.97---

Column 12, line 49: replace "5,06" with ---5.06---

Column 12, line 60: replace "benzhydryl" with ---Benzhydral---.

Column 13, line 14: replace "1,45" with ---1.45---.

Column 13, line 25: replace "C=N-" with ---CH=N- ---.

Column 13, line 35: replace "carboxylte" with ---carboxylate---.

Column 15, line 27: replace "cyclohxane" with ---cyclohexane---.

Column 16, line 35: replace "$CH_2OCCCH_3$" with ---$CH_2OCOCH_3$---.

UNITED STATES PATENT AND TRADEMARK OFFICE
CERTIFICATE OF CORRECTION

PATENT NO. : 4,071,681

DATED : January 31, 1978

INVENTOR(S) : HIROAKI YANAGISAWA et al

It is certified that error appears in the above-identified patent and that said Letters Patent are hereby corrected as shown below:

Column 17, line 3: replace "$CH_2COOCH_3$" with ---$CH_2OCOCH_3$---.

Column 17, line 43: replace "$CH_2COOCH_3$" with ---$CH_2OCOCH_3$---.

Column 18, line 59: replace "Pivalcyloxymethyl" with ---Pivaloyloxymethyl---.

Column 19, line 27: replace "CH=H" with ---CH=N---.

Column 20, line 45: replace "$OOOCH_3$" with ---$OCOCH_3$---.

Column 21, line 36: replace "CH" with ---OH---.

Column 22, line 52 (Claim 1): replace "panam" with ---penam---.

UNITED STATES PATENT AND TRADEMARK OFFICE
CERTIFICATE OF CORRECTION

PATENT NO. : 4,071,681
DATED : January 31, 1978
INVENTOR(S) : HIROAKI YANAGISAWA et al It is certified that error appears in the above-identified patent and that said Letters Patent are hereby corrected as shown below:

Column 11, line 20: replace "have" with ---base---.

Column 19, line 2: replace "NME" with ---NMR---.

Column 19, line 17: replace "metoxy" with ---methoxy---.

Column 23, line 6 (Claim 8): replace "contracted" with -- contacted --.

Signed and Sealed this

Seventeenth Day of October 1978

[SEAL]

Attest:

RUTH C. MASON
Attesting Officer

DONALD W. BANNER
Commissioner of Patents and Trademarks